United States Patent [19]

Huffman et al.

[11] Patent Number: 4,826,813
[45] Date of Patent: May 2, 1989

[54] 4'-METHYL-β-MERCAPTO-β,β-CYCLOPENTAMETHYLENEPROPIONIC ACID VASOPRESSIN ANTAGONISTS

[75] Inventors: William F. Huffman, Malvern; Nelson C. F. Yim, Ambler, both of Pa.

[73] Assignee: SmithKline Beckman Corporation, Philadelphia, Pa.

[21] Appl. No.: 52,809

[22] Filed: May 21, 1987

[51] Int. Cl.$^4$ .................. A61K 37/34; C07K 7/16
[52] U.S. Cl. ...................... 514/11; 514/807; 530/315
[58] Field of Search ............. 530/315; 514/11, 807

[56] References Cited

U.S. PATENT DOCUMENTS

| | | | |
|---|---|---|---|
| 4,367,225 | 1/1983 | Manning et al. | 530/315 |
| 4,469,679 | 9/1984 | Huffman et al. | 424/177 |
| 4,481,193 | 11/1984 | Ali et al. | 424/177 |
| 4,481,194 | 11/1984 | Ali et al. | 424/177 |
| 4,649,130 | 3/1987 | Manning et al. | 530/315 |
| 4,717,715 | 1/1988 | Ali | 530/315 |

OTHER PUBLICATIONS

"Carboxy Terminus of Vasopressin Required for Activity but Not Binding", Maurice Manning, Aleksandra Olma, Wieslaw Klis, Aleksander Kolodziejczyk, Eleonora Nawrocka, Aleksandra Misicka, Janny Seto & Wilbur H. Sawyer, Nature, vol. 380, 12 Apr. 1984, pp. 652–653.

"SK&F 101926 is Antidiuretic in Man"—Jeffrey Dubb, Nancy Allison, Dianne Tatoian, Alan Blumberg, Kenward Lee & Robert Stote, Kidney International, vol. 31, No. 1, 1987, p. 267.

"Synthesis of Arginine-Vasopressins, Modified in Positions 1 and 2, as Antagonists of the Vasopressor Response to the Parent Hormone", B. Lammek, P. Rekowski, G. Kupryszewski, P. Melin, U. Ragnarsson—Abstracts from the Tenth American Peptide Symposium, Washington University, St. Louis, MO, May 23–28, 1987.

"A Facile Synthesis of β-(S-benzylmercapto)-β,β-cyclopentamethylenepropionic Acid", W. Huffman, N. Yim–Int. J. Peptide Protein Res., 21, 1983, 568–570.

Moore et al., "Dicarbavasopressin Antagonist Analogues Exhibit Reduced in Vitro Agonist Activity", J. Med. Chem., 31, 1487–1489 (1987).

Albrightson et al., "Indomethocin (INDO) Unmasks Agonist Activity of the Vasopressin Antagonist, SK&F 101926 in Dogs", Fed. Proc., 46, 1284 (1987).

Stromberg et al., "Effects of Prostaglandin Inhibition on Vasopressin Levels in Women with Primary Dysmenorrhea", Obstet. Gynecol., 58, 206–208 (1981).

Aakerlund et al., "Inhibition of Vasopressin Effects on the Uterus by a Synthetic Analog", Obstet. Gynecol., (N.Y.), 309–312 (1983).

Primary Examiner—Delbert R. Phillips
Assistant Examiner—Christina Chan
Attorney, Agent, or Firm—Janice E. Williams; Stuart R. Suter; Alan D. Lourie

[57] ABSTRACT

Vasopressin antagonists which have a 4'-methyl-β-mercapto-β,β-cyclopentamethylenepropionic acid group have vasopressin antagonist activity without substantial agonist activity. A species of the invention is [1-(4'-methyl-β-mercapto-β,β-cyclopentamethylenepropionic acid)-2-(O-ethyl)-D-tyrosine-4-valine-8-arginine]vasopressin.

16 Claims, No Drawings

4'-METHYL-β-MERCAPTO-β,β-CYCLOPENTAMETHYLENEPROPIONIC ACID VASOPRESSIN ANTAGONISTS

FIELD OF THE INVENTION

This invention relates to cyclic peptide compounds which exhibit vasopressin antagonist activity and are substantially devoid of vasopressin agonist activity. This invention further relates to pharmaceutical compositions and methods for producing vasopressin antagonist activity without substantial agonist activity in patients in need thereof.

BACKGROUND OF THE INVENTION

The compounds of this invention exhibit $V_1$ and/or $V_2$ vasopressin antagonist activity without substantial agonist activity. Vasopressin is known to contribute to the antidiuretic mechanism of actions within the kidney. The action of these compounds antagonizes that of the natural anti-diuretic hormone (ADH) so as to cause the body to excrete water.

Manning et al., Nature 308, 652 (1984) has described the following compound

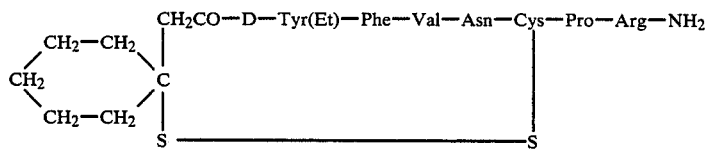

as having potent vasopressin antagonist activity. Also, this compound is reported as being devoid of detectable vasopressin agonist activity in vivo in rats. In man, however, this compound demonstrated only agonist activity (Dubb et al., Kidney Int. 31, 267 January 1987). A new test in dogs now shows that this compound does produce agonist activity.

The compounds of this invention have structures which are distinguished over the prior art in that there is a 4'-methyl substituent attached to the cyclopentamethylene propionic acid group and these compounds, while having vasopressin antagonist activity, are substantially devoid of agonist activity as shown by the test in dogs.

The effect of removal or replacement of amino acid groups in the tail of the peptide has been reported. Manning et al., Nature 308 652 (1984) and U.S. Pat. No. 4,469,679 have disclosed that the terminal glycine unit at the 9-position of certain 1-(β-mercapto β,β-cyclopentamethylene propionic acid) vasopressin compounds can be removed or replaced by L or D-Ala, Ser or Arg without necessarily affecting the binding at vasopressin receptors.

U.S. Pat. Nos. 4,481,194 and 4,481,193 have disclosed that removing proline at position 7 or both proline and glycine at positions 7 and 9 from the structures of vasopressin antagonist compounds will produce compounds which retain substantial, but somewhat reduced, antagonist activity.

DESCRIPTION OF THE INVENTION

The compounds of this invention are illustrated by the following structural formula:

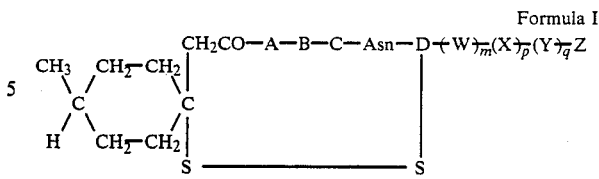

A is D or L isomer of Phe, Phe(4'-Alk), Ile, Cha, Tyr, or Tyr(O-Alk);
B is Phe, Phe(4'-Alk), Tyr(O-Alk), Ile or Tyr; C is Val, Ile, Abu, Chg, Gln, Lys, Cha, Nle, Leu, Ala or Gly;
D is D or L isomer of Cys;
m, p and q are each 0 or 1;
W is D or L isomer of Pro, Arg, HArg, N-MeArg, Lys or Orn;
X is D or L isomer of Arg, Lys, Orn or Gln or when m is 1, X may be Gly;
Y is D or L isomer of Arg, Lys, Orn, Ser, Gln, Tyr or Ala or when at least one of m or p is 1, Y may be Gly;
Z is $NH-(CH_2)_n-NHR$, or a D or L isomer of $Arg-NH_2$, $Lys-NH_2$ or $Orn-NH_2$ or when at least one of m, p and q is 1, Z may be NHR' or OH;
R is H or $C(=NH)-NH_2$;
R' is H or Alk;
n is 2-6; and
Alk is alkyl having 1-4 carbon atoms;
or a pharmaceutically acceptable acid addition salt, or lower alkyl or benzyl ester thereof.

In the preparation of the compounds of this invention as described hereinafter, a major isomer of the 4'-methylcyclopentamethylene propionic acid intermediate is formed in about 80–90% yield. This isomer is used to prepare the corresponding isomer of compounds of formula I which have potent vasopressin antagonist activity and are substantially devoid of agonist activity. The minor isomer has more agonist activity. The major isomer is believed to be the cis isomer; cis being defined as the 4'-methyl and the sulfur atom being on the same side of the cyclohexane ring.

Particularly, this invention relates to the cis isomers of the compounds of formula I.

A subgeneric group of compounds of this invention are compounds of formula I in which:
A is D Tyr or D Tyr(Et);
B is Phe;
C is Val;
m, p and q are each 0 or 1;
W is a D or L isomer of Pro, Arg or N-MeArg;
X is a D or L isomer of Arg or Gly;
Y is Gly; and
Z is NHR or a D or L isomer of $Arg-NH_2$.

Particular $(W)_m-(X)_p-(Y)_q-Z$ tails are $Pro-Arg-NH_2$, $Arg-Gly-NH_2$, $Pro-Arg-Gly-NH_2$, Arg D-$Arg-NH_2$, D-Arg-D-$Arg-NH_2$, $Pro-NH(CH_2)_4NHC-(=NH)-NH_2$, N-MeArg—Arg—NH₂, Pro—Arg—NH(CH₂)₂NH₂, Arg—NH₂, and Arg—Gly—Arg—NH₂.

Particular compounds of this invention are [cis-1-(4'-methyl-β-mercapto-β,β-cyclopentamethylene-propionic acid)-2-(O-ethyl)-D-tyrosine-4-valine-8-arginine-9 desglycine-]-vasopressin, [cis-1-(4'-methyl-β-mercapto-β,β-cyclopentamethylene-propionic acid)-2 -(O-ethyl)-D-tyrosine-4-valine-8-arqinine]-vasopressin, [cis-1-(4'-methyl-β-mercapto-β,β-cyclopentamethylene-propionic acid)-2-(O-ethyl)-D-tyrosine-4-valine-7-arginine-8-D-arginine-9-desglycine]-vasopressin.

Also included in this invention are addition salts, complexes or prodrugs, such as esters of the compounds of this invention when Z is OH, and especially the non-toxic, pharmaceutically acceptable acid addition salts. The acid addition salts are prepared in standard manner in a suitable solvent from the parent compound and an excess of an acid, such as hydrochloric, hydrobromic, sulfuric, phosphoric, acetic, maleic, succinic, ethane-disulfonic or methanesulfonic acids. The ester derivatives of the acid form of the end products, such as the methyl, ethyl or benzyl esters, are prepared as known in the art.

In the description herein and in the claims, the nomenclature common in the art of peptide and vasopressin chemistry is used. When no configuration is noted, the amino acid unit is in the L, or naturally occurring, form. In certain structural formulas, such as Cys, the thio members are added for clarity.

The peptide art designations contained herein include the following: Pmp, β-mercapto-β,β-cyclopentamethylenepropionic acid; Abu, α-amino-n-butyric acid; Chg, cyclohexylglycine; Cha, cyclohexylalanine; Gln, glutamic acid amide or glutamine; Gly, glycine; Tyr, tyrosine; Phe, phenylalanine; Val, valine; Ile, isoleucine; Nle, norleucine; Leu, leucine; Ala, alanine; Lys, lysine; Arg, arginine; HArg, homoarginine; Orn, ornithine; Ser, serine; VSP, vasopressin; Tos, tosylate; Bzl, benzyl; MBzl, p methoxybenzyl; Boc, t-butoxycarbonyl; ClZ, chloro 2 -benzyloxycarbonyl; DMAP/DCC, dimethylaminopyridine/dicyclohexylcarbodiimide.

"Alk" represents a lower alkyl of 1 to 4 carbons. Such alkyl substituents include methyl, ethyl, n-propyl, isopropyl or butyl. The preferred alkyl substituent is ethyl.

The compounds of formula I are prepared by cyclizing a linear peptide by means of the two mercapto groups at the cysteine unit at position 6 and the 4'-methyl-β-mercapto-β,β-cyclopentamethylenepropionic acid (4'-MePmp) at position 1. The cyclization reaction occurs in the presence of a mild oxidizing agent capable of oxidizing a mercaptan to a disulfide. Thus, linear peptides of the following formula are oxidized:

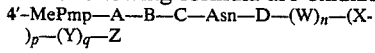
)ₚ—(Y)_q—Z        Formula II in which A,B,C,D,W,X,Y,Z,m,p and q are as defined in formula I, with the mercapto groups being members of the 4'-MePmp and D units.

The oxidation is carried out using, for example, an excess of an alkali metal ferricyanide, such as potassium or sodium ferricyanide. A suitable unreactive solvent, preferably an aqueous solvent at neutral pH, about 7-7.5, is used. The reaction is carried out at ambient temperature or lower until the reaction is substantially complete. Preferably, low concentrations of the linear peptide dimercaptan and the oxidizing agent are used, such as about 0.01 to 0.1 molar concentration of oxidizing agent in several liters of aqueous solution to cyclize about 1-5 grams of dimercaptan.

Other mild oxidation agents having an oxidation potential roughly equivalent to ferricyanide may also be used for the ring closure reaction such as passing oxygen through the reaction solution for several days. In addition, iodine in methanol can be used on the unprotected peptide or the acetamidomethyl sulfur-protected derivative. Cyclization, also, occurs when a displaceable, thiol-protective group such as that at the mercaptan group of the 4'-MePmp unit is displaced intramolecularly.

Of course, one skilled in the art would recognize that when an interfering reaction site is present in the structure of the starting material of formula II, the linear mercaptan starting material may have common protective groups temporarily present at the various amino acid units.

The compounds of formula I in which Z is NH—(CH₂)_m—NHR are conveniently prepared by the following procedure:

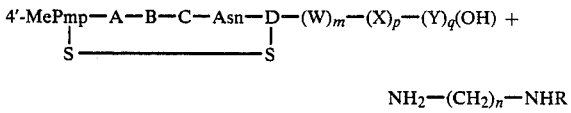

NH₂—(CH₂)_n—NHR as described by Callahan et al., U.S. Pat. No. 4,543,349 and in examples herebelow.

The peptides of formula I are conveniently isolated by acidifying the aqueous oxidation mixture, such as using glacial acetic acid, and passing the reaction mixture over an ion exchange chromatographic column, for example, over a weakly acid, acrylic resin column with elution using buffered base, or by gel filtration over a bead-formed gel prepared by cross linking dextran with epichlorohydrin.

The intermediates of formula II, in free or protected form, are conveniently prepared using solid-phase methods of peptide synthesis as discussed in Manning et al., J. Med. Chem. 25, 46 (1982). A commercial benzhydrylamine support resin (BHA) is used to prepare the amide end products of formula I, and a chloromethyl support resin (CMR) is used to prepare the acid compounds of formula I, i.e. in which Z is OH. Solution or enzymatic synthetic methods can also be used.

The peptide chain of the linear peptides is usually built up, stepwise, proceeding from the last unit (in the 7,8,9 or 10 positions) and working toward the 4'-MePmp unit. Each unit is properly protected as known in the peptide art and as described below. The sequence of step-reactions is conveniently carried out in a Beckman 990B peptide synthesizer or its equivalent without isolation of each intermediate peptide. The details of the procedure are in the examples presented hereinafter.

The various amino acids, which are consecutively added to the resin-supported chain, are protected as known in the art. For example, the t-butoxycarbonyl protecting group may be used for an amino group, especially at the α-position; an optionally substituted benzyl or acetamidomethyl for the mercapto groups at the 4'-MePmp or Cys units; tosyl for the Arg, HArg or N MeArg unit; and an optionally substituted benzyloxycarbonyl for the Tyr or Lys units. The protective groups are, most conveniently, those which are not easily removed by using mild acid treatment. It is preferable to use protective groups that are removed using sodium-liquid ammonia or, for benzyl or benzyloxycarbonyl groups, catalytic hydrogenation. Other protective groups are known to the art, such as those noted in "Protective Groups in Organic Chemistry" by J. F. W. McOmie (Plenum 1973).

The protected linear peptide intermediate is split from the carrying resin matrix, for example, by using ammonia in an aqueous miscible solvent, and, then, is treated to remove the protective groups, such as by using sodium liquid ammonia. This procedure gives the amide derivative of the linear peptide intermediate.

More conveniently, the two steps are combined by treating the resin supported peptide with anhydrous hydrogen fluoride using a suitable carbonium ion scavenger, such as anisole, to give the linear peptide intermediate of formula II.

The 4'-MePmp intermediate, protected with benzyl on the mercapto group, is prepared by reacting ethyl 4'-methylcyclohexylidene acetate with benzylmercaptan by the procedure described by Yim and Huffman, Int. J. Peptide Protein Res. 21, 568 (1983) for the preparation of the desmethyl compound, $\beta$-(S-benzylmercapto)-$\beta,\beta$-cyclopentamethylenepropionic acid. The major isomer obtained in this preparation is purified by recrystallization from a suitable solvent such as hexane.

The compounds of formula I have $V_1$ and/or $V_2$ vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. The mechanism of action is at the vasopressin receptors ($V_2$-receptors) located on the plasma membrane of certain renal epithelial cells. The most notable pharmacodynamic effect of the ADH antagonists of this invention is that of a water diuretic, or aquaretic, rather than of a natriuretic such as hydrochlorothiazide.

$V_2$-antagonistic activity toward the natural anti-diuretic hormone (anti-ADH activity) is determined, in vitro, in the medullary tissue of hog or human kidneys and, in vivo, in the hydropenic rat. The in vitro assay procedures for vasopressin stimulated adenylate cyclase activation or vasopressin binding activity are described by F. Stassen et al., J. Pharmacology and Experimental Therapeutics 223, 50-54 (1982). $V_1$-antagonistic activity is determined by procedures using the rat thoracic aorta tissue and plasma membranes of rat liver. These procedures are described in the noted Stassen publication and in a publication at the 1st International Conference on Diuretics, Miami, Fla., March (1984). Oxytocin antagonism is determined as described by W. Sawyer et al., Endocrinology 106, 81 (1979).

A patient suffering from the syndrome of inappropriate antidiuretic hormone condition or from an undesirable edematous condition is a target for the compounds of this invention. Examples of clinical conditions for which the compounds of this invention may be used include hypertension, hepatic cirrhosis, hyponatremia, congestive heart failure or a component, such as edema, of any traumatic condition resulting from serious injury or disease.

The second group of vasopressin receptor sites are the vascular pressor sites ($V_1$-receptors) within the cardiovascular system itself. These may also be antagonized by the compounds of this invention.

The compounds of this invention are also oxytocin antagonists and as such are useful to prevent premature labor and in the treatment of primary dysmenorrhea.

The compounds of this invention, therefore, are used especially to induce anti-hypertensive, anti-oxytocic or diuretic activity in patients in need of such treatment. The compounds are administered internally, parenterally, buccally or by insufflation, in a nontoxic but effective quantity, preferably dispersed in a pharmaceutical carrier. Dosage units of the active ingredient are selected from the range of about 0.01 to about 10 mg/kg, preferably about 0.1 to about 1 mg/kg, of base based on a 70 kg patient. The dosage units are administered to the human or animal patient from about 1 to about 5 times daily.

Pharmaceutical compositions which contain an active antaqonist ingredient of formula I, comprise a dosage unit which is dissolved or suspended in a standard liquid carrier, such as isotonic saline, and is contained in an ampoule or multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparations, gels, buffers for isotonic preparations, buccal losenges, trans dermal patches and emulsions or aerosols.

For compounds of this invention, antagonist activity toward the natural antidiuretic hormone (anti-ADH activity) is demonstrated, in vivo, in the hydropenic rat and, in vitro, in the medullary tissue of hog kidney. The hydropenic rat screen and the hog kidney assay are known to the art, Huffman et al., U.S. Pat. No. 4,469,679.

TABLE I

4'-MePmP—A—Phe—Val—Asn—Cys—Pro—Arg—Q
  |                              |
  S——————————————————————————————S

| Compound* | | Rat in vivo | Pig in vitro | |
|---|---|---|---|---|
| A | Q | ED$_{300}$($\mu$g/kg) | K$_i$(nM) | K$_{bind}$(nM) |
| L—Tyr(Me) | Gly—NH$_2$ | 165 | 44 | 130 |
| D—Tyr(Et) | NH$_2$ | 45 | — | 19 |
| D—Tyr(Et) | Gly—NH$_2$ | 13 | 4.2 | 13 |

*All compounds have cis isomer of 4'-MePmP

The compounds are tested fo partial agonist activity by the following procedures:

PARTIAL AGONIST SCREEN

Food is removed from female mongrel dogs approximately 18 hours prior to testing. The studies are conducted under steady state water diuresis initiated by a 5% body weight water load and a 3% dextrose infusion. At 0 hour, indomethacin, a cyclooxygenase inhibitor, is administered (2 mg/kg i.v. bolus and 3 mg/kg/hr i.v. infusion). Twenty minutes later, the test compound is administration i.v. Urine volume and osmolality are measured every 10 minutes for 4 hours.

TABLE II

R—D—Tyr(Et)—Phe—Val—Asn—Cys—Pro—Arg—Q
|                                          |
S————————————————————S

| Compound# | osmolality (mOsm/kg H₂O)* control | +INDO | volume (ml/min)* control | +INDO |
|---|---|---|---|---|
| none | 43 | 86 | 5.7 | 3.1 |
| ADH (3 ng/kg) | 598 | 939 | 0.16 | 0.02 |
| R = Pmp, Q = NH₂ | 284 | 1419 | 1.2 | 0.15 |
| R = 4'-MePmp, Q = NH₂ | — | 70 | — | 2.0 |
| R = Pmp, Q = Gly—NH₂ | — | 399 | — | 0.55 |
| R = 4'-MePmp, Q = Gly—NH₂ | — | 72 | — | 3.3 |

*Three hours post dosing with compound (ADH, peptide analog).
Unless otherwise indicated, all analogs were tested at 100 μg/kg. All 4'-MePmp analogs contained the cis orientation.

The table of biological test results presented above demonstrates that treatment with indomethacin potentiates the antidiuretic activity (i.e. increases urine osmolality and decreases volume) of ADH and potentiates the partial agonist activity of the des-methyl compound (R=Pmp and Q=NH₂) such that it subsequently behaves as an agonist. This finding is critical since, in man, the Pmp compound (Q=NH₂) demonstrated only agonist activity (Dubb et al., Kidney Int. 31, 267, January 1987) a property which was not observed in all animal models previously tested. The indomethacin dog model may predict the agonist activity of a compound in man. The finding that the 4'-MePmp analogs do not possess partial agonist activity in this sensitive bioassay system indicates that unexpected advantageous properties of the 4'-MePmp compounds as compared to the Pmp compound.

The following examples are not limiting but are illustrative of the invention. All temperatures are in degrees centigrade.

EXAMPLE 1

Preparation of 4'-Methyl-β-benzylmercapto-β,β-cyclopentamethylenepropionic acid [4'-MePmp(Bzl)] and the corresponding 4-methylbenzylmercapto compound [4'-MePmp(4 MeBzl)]

To a mixture of 200 ml of toluene and 20.5 g of sodium hydride (59% in mineral oil) was added 119.8 g of triethyl phosphonoacetate, keeping the temperature below 30–35°. The mixture was stirred at room temperature for 2 hours. 4-Methylcyclohexanone (50 g) was added slowly while maintaining a temperature of 25° (some cooling needed). The mixture was stirred at room temperature for 32 hours and then poured over water. The organic layer was washed with brine, then concentrated and distilled to give ethyl 4-methylcyclohexylideneacetate.

To a mixture of 200 ml of toluene and 11.1 ml of benzyl mercaptan was added 0.5 g of sodium hydride (59% in mineral oil) and the resulting mixture was stirred for 30 minutes, then treated with dry dimethylformamide and stirred at room temperature for 15 minutes. Ethyl 4-methylcyclohexylideneacetate (9.1 g) was added and the solution was stirred for 1.5 hours, then allowed to stand at room temperature overnight. The mixture was poured over water and extracted with ether. The organic extracts were washed with brine, then evaporated with an aspirator to give ethyl 4'-methyl-β-benzylmercapto-β,β-cyclopentamethylenepropionate. To this ester was added 100 ml of water, 300 ml of methanol and 50 g of potassium carbonate. The mixture was refluxed for 20 hours. Methanol was evaporated off; water was added; the aqueous layer was washed with 1:1 hexane, ethyl acetate and then acidified with hydrochloric acid to pH 2. Extracting with ether, washing the ether extract with brine and drying over magnesium sulfate, concentrating the organic solution and recrystallizing from hexane gave 4'-methyl-β-benzylmercapto-β,β-cyclopentamethylenepropionic acid, m.p., 75°–76°. Recrystallization from dichloromethane/hexane gave the cis isomer of 4'-methyl-β-benzylmercapto-β,β-cyclopentamethyleneproprionic acid.

By the same procedure, using 4-methylbenzyl mercaptan in place of benzyl mercaptan, 4'-methyl-β-(4-methylbenzylmercapto)-β,β-cyclopentamethylenepropionic acid, m.p. 92°–94°, was obtained. Recrystallization from hexane qave the cis isomer.

EXAMPLE 2

The vasopressin antagonist compound [1-(4'-methyl-β-mercapto-β,β-cyclopentamethylenepropionic acid)-2-(O-ethyl)-D-tyrosine-4-valine-8-arginine-9-desglycine]-vasopressin is represented by the following structural formula:

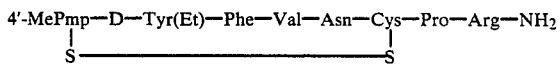

4'-MePmp—D—Tyr(Et)—Phe—Val—Asn—Cys—Pro—Arg—NH₂
|                                        |
S————————————————————S

The protected peptide-resin intermediate, 4'-MePmp(4-MeBzl)-D-Tyr(Et)-Phe-Val-Asn-Cys(4-MeBzl)-Pro-Arg(Tos)-BHA, is synthesized by solid phase methods on the automated synthesizer Beckman 990 B using 1.0 g of benzhydrylamine resin (approx. 0.62 mmol). All amino acids are protected as t-butyloxycarbonyl (Boc) on the nitrogen and are activated by DCC/HBT for sequential coupling. The 4'-MePmp (4-MeBzl) is coupled using DMAP/DCC. The peptide is cleaved from the resin with simultaneous deprotection of the side chain protecting qroups using anhydrous HF (30 ml) in the presence of anisole (3.0 ml) at 0° C. for 60 minutes. After evaporation in vacuo to dryness, the residue containing peptide is washed with anhydrous ether. The crude peptide is extracted with dimethylformamide (100 ml) and 40% acetic acid (100 ml) into 3.5 liters of degassed water which has been adjusted to a pH of 4.5. The aqueous diluted disulfhydryl octapeptide mixture is oxidatively cyclized with 110 ml of potassium ferricyanide (0.01M) at a pH of 7.2. The pH of the solution is adjusted to 4.5 using glacial acetic acid. The solution is passed through a weakly acid acrylic resin (Bio-Rex 70) column. The column is eluted with pyridine-acetate buffer (30:4:66, pyridine/glacial acetic acid/water v/v). The pyridine acetate was removed by distillation in vacuo. The residue is lyophilized from dilute acetic acid to give the product of partially purified crude peptide.

Purification:

Preparative high pressure liquid chromatography (HPLC) using 5μ ultrasphere ODS (60% H₂O/0.1% TFA, 40% CH₃CN/0.1% TFA) to yield 13 mg (2.38%) pure product. The product was confirmed by FAB-MS [(M+H)+=1093] and Amino Acid Analysis (Asp=1.0; Val=0.85; Tyr=0.90; Phe=0.83; Arg=0.98). The purity was confirmed by HPLC (5μ Ultrasphere ODS, 4.6 mm×250 mm, 60% H₂O/0.1% TFA; 40% CH₃CN/0.1% TFA, K'=8, gradient 80:20 to 50:50

0.1% aqueous TFA/CH₃CN K'=11.8) and TLC Butanol:Acetic Acid:Water (4:1:1) $R_f$=0.538, Butanol:Ethyl Acetate:Acetic Acid:Water (1:1:1:1) $R_f$=0.676.

EXAMPLE 3

The vasopressin antagonist compound [1-(4'-methyl-β-mercapto-β,β-cyclopentamethylene propionic acid)-2-(O-ethyl)-D-tyrosine-4-valine-8-arginine]-vasopressin is represented by the following structural formula:

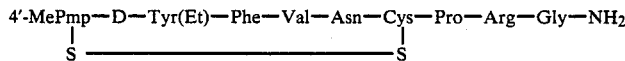

The protected peptide-resin intermediate, 4'-MePmp(Bzl)-D-Tyr(Et)-Phe-Val-Asn-Cys(MBzl)-Pro-Arg(Tos)-Gly-Resin, was prepared from Boc-Gly resin (3 mM/5.4 grams of resin). The appropriately protected amino acids (all amino acids are protected as t-butyloxycarbonyl on the alpha-nitrogen) were coupled sequentially onto the Boc-Gly resin, prepared by reacting Boc-Gly as the cesium salt with commercial Merrifield resin (Cl—CH₂ —resin) as known to the art, by using a manual program as described in the following steps.
1. washed with methylene chloride (3 times, 1 minute).
2. prewashed with 33% trifluoroacetic acid in methylene chloride with 1% indole (1 time, 1 minute)
3. deprotection with 33% trifluoroacetic acid in methylene chloride with 1% indole (20 minutes).
4. washed with methylene chloride (1 time, 1 minute).
5. washed with ethanol (1 time, 1 minute).
6. washed with methylene chloride (2 times, 1 minute).
7. prewashed with 10% triethylamine in methylene chloride (1 time, 1 minute).
8. neutralization with 10% triethylamine in methylene chloride (10 minutes).
9. protected amino acid (10 mM) in triethylamine in methylene chloride and 0.5 M N,N'-dicyclohexylcarbodiimide in methylene chloride (20 ml) were added and the reaction time was up to two hours.

In the case of the coupling of the Asn moiety, 1 -hydroxybenzotriazole (HBT, 10 mM) was added with Boc-Asn in dry dimethylformamide. Completion of each coupling reaction was monitored by the ninhydrin test. The p-methoxybenzyl group was used to protect the thiol group of Cys and the 4'-MePmp(Bzl) is coupled using DMAP/DCC.

4'-MePmp(Bzl)-D-Tyr(Et)-Phe-Val-Asn-Cys(MBzl)-Pro-Arg(Tos)-Gly-Resin (4 g, ca. 1.5 mM) was subjected to ammonolysis using saturated ammonia/methanol solution (200 ml) at room temperature for 48 hours. After evaporation to almost dryness, the residue was extracted with DMF. The combined extracts were concentrated to approximately 5 ml and ether was added to precipitate the peptide which was collected and dried. This crude peptide was dissolved in liquid ammonia (250 ml) and treated with sodium/liquid ammonia solution to give 4'-MePmp-D-Tyr(Et)-Phe-Val-Asn-Cys-Pro-Arg-Gly-NH₂. The crude peptide is dissolved in 3.5 liters of degassed water containing 10 ml qlacial acetic acid and the mixture is adjusted to pH 7.2 with NH₄OH. The aqueous diluted disulfhydryl nonapeptide solution is oxidatively cyclized with 110 ml of potassium ferricyanide (0.01 M) at a pH of 7.2. The solution is adjusted to pH 4.5 using glacial acetic acid. The solution is passed through a weakly acid acrylic resin (Bio-Rex 70) column. The column is eluted with pyridine-acetate buffer (30:4:66, pyridine/glacial acetic acid/water v/v). The pyridine acetate was removed by distillation in vacuo. The residue is lyophilized from dilute acetic acid to give the product of partially purified crude peptide.

Purification:
1. CCD Partition using 4:1:5 (BuOH:HOAc:H₂O)
2. Gel-filtration:Sephadex G-15, 0.2 M HOAc Physical Data:
Yield: 83 mg from 1 mmole of Boc-Gly resin (7%)
A.A. cont: 67% by A.A. analysis; 88% by nitrogen analysis
A.A. analysis: Asp (0.92), Pro (1.02), Gly (1.00); Cys (0.56), Val (0.94), Tyr (0.57), Phe (0.92), Arg (0.88).
FAB M.S.: (M+H)⁺ 1150, (M−H)⁻ 1148
M.F.: $C_{54}H_{79}N_{13}O_{11}S_2$
M.W.: 1150.420
HPLC: >95% pure using the following gradient system 80/20→50/50 in 20 mins of H₂O/CH₃CN (0.1% TFA); a 5μ C-18 column
TLC: 1:1:1:1, BuOH:HOAc:EtOAc:H₂O $R_f$=0.66

EXAMPLE 4

The vasopressin antagonist compound [1 -(4'-methyl-62 -mercapto-β,β-cyclopentamethylene propionic acid)-2-(O-ethyl)-D-tyrosine-4-valine-7-arginine-8-glycine-9-glycine-10-arginine]-vasopressin is represented by the following structural formula:

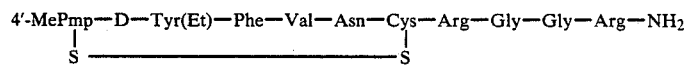

The protected peptide resin intermediate, 4'-MePmp(4-MeBzl)-D-Tyr(Et)-Phe-Val-Asn-Cys(4 MeBzl)-Arg(Tos)-Gly-Gly-Arg(Tos)-BHA, is synthesized by solid-phase methods on the automated synthesizer Beckman 990 B 1.0 g of benzhydrylamine resin (approx. 0.62 mmol). All amino acids are protected as t-butyloxycarbonyl on the nitrogen and are activated by DCC/HBT for sequential coupling. The 4'-MePmp(4-MeBzl) is coupled using DMAP/DCC. The peptide is cleaved from the resin with simultaneous deprotection of the side chain protecting groups using anhydrous HF (30 ml) in the presence of anisole (3.0 ml) at 0° C. for 60 minutes. After evaporation in vacuo to dryness, the residue containing peptide is washed with anhydrous ether. The crude peptide is extracted with dimethylformamide (100 ml) and 40% acetic acid (100 ml) and the extracts are added to 3.5 liters of degassed water. The aqueous diluted disulfhydryl decapeptide mixture is oxidatively cyclized with 110 ml of potassium ferricyanide (0.01M) at a pH of 7.2. The pH of the solution is adjusted to 4.5 using glacial acetic acid. The solution is passed through a weakly acid acrylic resin (Bio-Rex 70) column. The column is eluted with pyridine-acetate buffer (30:4:66, pyridine/glacial acetic acid/water v/v).

The pyridine acetate was removed by distillation in vacuo. The residue is lyophilized from dilute acetic acid to give the product of partially purified crude peptide.

EXAMPLE 5

The vasopressin antagonist compound [-1-(4'-methyl-β-mercapto-β,β-cyclopentamethylene propionic acid)-2-(O-ethyl)-D-tyrosine-4-valine-6-D-cysteine-7-N-methylarginine-8-arginine-9-desglycine]-vasopressin is represented by the following structural formula:

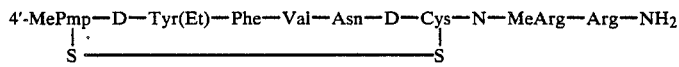

The protected peptide-resin intermediate, 4'-MePmp(4-MeBzl)-D-Tyr(Et)-Phe-Val-Asn-D-Cys(4-MeBzl)-N-MeArg(Tos)-Arg)TOS)-BHA, is synthesized by solid phase methods on the automated synthesizer Beckman 990 B using 1.0 g of benzhydrylamine resin (approx. 0.62 mmol). All amino acids are protected as t-butyloxycarbonyl on the nitrogen and are activated by DCC/HBT for sequential coupling. The 4'-MePmp(4-MeBzl) is coupled using DMAP/DCC. The peptide is cleaved from the resin with simultaneous deprotection of the side chain protecting groups using anhydrous HF (30 ml) in the presence of anisole (3.0 ml) at 0° C. for 60 minutes. After evaporation in vacuo to dryness, the residue containing peptide is washed with anhydrous ether. The crude peptide is extracted with dimethylformamide (100 ml) and 40% acetic acid (100 ml) and the extracts are added to 3.5 liters of degassed water. The aqueous diluted disulfhydryl octapeptide mixture is oxidatively cyclized with 110 ml of potassium ferricyanide (0.01M) at a pH of 7.2. The pH of the solution is adjusted to 4.5 using glacial acetic acid. The solution is passed through a weakly acid acrylic resin (Bio-Rex 70) column. The column is eluted with pyridine acetate buffer (30:4:66, pyridine/glacial acetic acid/water v/v). The pyridine acetate was removed by distillation in vacuo. The residue is lyophilized from dilute acetic acid to give the product of partially purified crude peptide.

EXAMPLE 6

The vasopressin antagonist compound [1-4'-methyl-β-mercapto-β,β-cyclopentamethylene propionic acid)-2-(O-ethyl)-D-tyrosine-4-valine-7-arginine-8-desarginine-9-desglycine]-vasopressin is represented by the following structural formula:

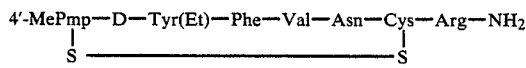

The protected peptide resin intermediate, 4'-MePmp(4MeBzl)-D-Tyr(Et)-Phe-Val-Asn-Cys(-4MeBzl)-Arg(Tos)-BHA, is synthesized by solid phase methods on the automated synthesizer Beckman 990 B using 1.0 g of benzhydrylamine resin (approx. 0.62 mmol). All amino acids are protected as t-butyloxycarbonyl on the nitrogen and are activated by DDC/HBT for sequential coupling. The 4'-MePmp(4-MeBzl) is coupled using DMAP/DCC. The peptide is cleaved from the resin with simultaneous deprotection of the side-chain protecting groups using anhydrous HF (30 ml) in the presence of anisole (3.0 ml) at 0° C. for 60 minutes. After evaporation in vacuo to dryness, the residue containing peptide is washed with anhydrous ether. The crude peptide is extracted with dimethylformamide (100 ml) and 40% acetic acid (100 ml) and the extracts are added to 3.5 liters of degassed water. The aqueous diluted disulfhydryl heptapeptide mixture is oxidatively cyclized with 110 ml of potassium ferricyanide (0.01M) at a pH of 7.2. The pH of the solution is adjusted to 4.5 using glacial acetic acid. The solution is passed through a weakly acid acrylic resin (Bio-Rex 70) column. The column is eluted with pyridine acetate buffer (30:4:66), pyridine/glacial acetic acid/water v/v). The pyridine acetate was removed by distillation in vacuo. The residue is lyophilized from dilute acetic acid to give the product of partially purified crude peptide.

EXAMPLE 7

The vasopressin antagonist compound [1(4'-methyl-β-mercapto-β,β-cyclopentamethylene propionic acid)-2-(O-ethyl)-D-tyrosine-4-valine-7-arginine-8-D-arginine-arginine-9-desglycine]-vasopressin is represented by the following structural formula:

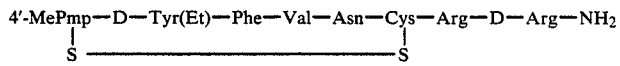

The protected peptide resin intermediate, 4'-Mepmp(4MeBzl)-D-Tyr(Et)-Phe-Val-Asn-Cys(4-MeBzl)-Arg(Tos)-D-Arg(Tos)-BHA, is synthesized by solid-phase methods on the automated synthesizer Beckman 990 B using 1.0 g of benzhydrylamine resin (approx. 0.62 mmol). All amino acids are protected as t-butyloxycarbonyl on the nitrogen and are activated by DCC/HBT for sequential coupling. The 4-MePmp(4-MeBzl) is coupled using DMAP/DCC. The peptide is cleaved from the resin with simultaneous deprotection of the side-chain protecting groups using anhydrous HF (30 ml) in the presence of anisole (3.0 ml) at 0° C. for 60 minutes. After evaporation in vacuo to dryness, the residue containing peptide is washed with anhydrous ether. The crude peptide is extracted with dimethylformamide (100 ml) and 40% acetic acid (100 ml) and the extracts are added to 3.5 liters of degassed water. The aqueous diluted disulfhydryl octapeptide mixture is oxidatively cyclized with 110 ml of potassium ferricyanide (0.01 M) at a pH of 7.2. The pH f the solution is adjusted to 4.5 using glacial acetic acid. The solution is passed through a weakly acid acrylic resin (Bio-Rex 70) column. The column is eluted with pyridine acetate buffer (30:4:66, pyridine/glacial acetic acid/water v/v). The pyridine acetate was removed by distillation in vacuo. The residue is lyophilized from dilute acetic acid to give the product of partially purified peptide.

EXAMPLE 8

Preparation of:

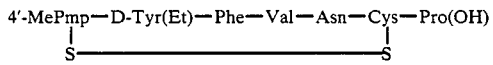

Boc-Pro-Merrifield resin is made by coupling Boc-Pro to Merrifield resin using the cesium salt method to give Boc-Pro-OCH$_2$C$_6$H$_4$-resin which is used as the starting material for the synthesis. The synthesis is carried out on the Beckman 990 B peptide synthesizer using the following protocol. Three equivalents of the amino acids are dissolved in their appropriate solvents [the Boc derivatives of Cys(MeBzl), Val, Phe and 4'-MePmp(MeBzl) in methylene chloride, Asn in dimethylformamide, X such as D-Tyr(Et) or BrZ-D-Tyr in 1:1 methylene chloride/dimethylformamide] and are coupled using an equimolar amount of dicyclohexylcarbodiimide (DCC) and 1-hydroxybenzotriazole (HBT) except for the coupling of 4'-MePmp (4-MeBzl) where 1.0 equivalent of dimethylaminopyridine is used as catalyst. The extent of coupling is determined by qualitative ninhydrin analyses of each aliquot sample and couplings are repeated when necessary. The Boc groups are removed using 1:1 trifluoroacetic acid/methylene chloride and, after washing, the free amine is generated using 5% diisopropylethylamine/methylene chloride. The sequence of the peptide is checked using solid phase sequencing before the coupling of the 4'-MePmp(4-MeBzl) and its homogeneity confirmed.

1.1 Grams (0.5 mmole) of the protected heptapeptide resin with 3 ml of anisole is stirred 60 min at 0° (ice bath) in 25 ml of anhydrous liquid hydrogen fluoride (HF). The HF is then removed under reduced pressure at 0°. The residue is washed with ethyl ether (4×20 ml, discarded) and the peptide extracted with dimethylformamide (3×10 ml), 20% acetic acid (3×10 ml) and 0.3N ammonium hydroxide (3×10 ml).

The extracts are added to 2 l of degassed water and pH adjusted to 7.1 with conc. ammonium hydroxide. A 0.01M solution of potassium ferricyanide is then added dropwise with stirring until a faint yellow color persisted (41 ml). The solution is adjusted to pH 4.5.

The resulting solution is then passed through a flash column (5 cm×15 cm) of a packing of silica gel coated with a C-18 silane. The column is then washed with 350 ml of water and the peptide eluted with 500 ml of 1:1 acetonitrile/water (0.25% trifluoroacetic acid) in 20 ml fractions.

The appropriate fractions are combined and concentrated. The residue is dissolved in conc. acetic acid, diluted with water and lyophilized to give the title peptide which is used without further purification for the synthesis of the tail modified peptides.

EXAMPLE 9

Preparation of:

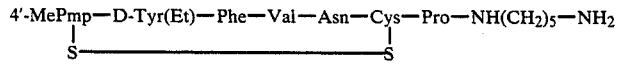

1,5-Diaminopentane (14.0 ml, 120 mmol) was dissolved in tert.-butanol(70 ml) and was treated dropwise over a period of 10 min with di-tert-butyl dicarbonate (9.2 ml, 40 mmol). After the addition had been completed, the reaction mixture was stirred at room temperature for 16.5 hr. The reaction was then treated with 1N sodium hydroxide solution (aq) (90 ml), stirred for 1 hr and finally extracted with chloroform. The chloroform extracts were dried (MgSo$_4$) and concentrated under vacuum. The residue was dissolved in water, made acidic (pH=2) by the dropwise addition of 3N hydrochloric acid at 0° and was washed with ether to remove the diprotected diamine. The aqueous portion was made basic (pH 10) with 5% sodium carbonate solution and was extracted with ethyl acetate to give 1.6 g (20%) of mono-Boc 1,5-diaminopentane. The structure was confirmed by $^1$H NMR and CI-MS.

To a solution of the heptapeptide prepared in Example 8 and mono-Boc-1,5-diaminopentane in dimethylformamide, dicyclohexylcarbodiimide and 1-hydroxybenzotriazole hydrate is added. The reaction mixture is stirred at room temperature for 19 hours. The dimethylformamide is then removed under vacuum. The residue is treated with trifluoroacetic acid at 0° for 2 hours. After this time, the trifluoroacetic acid is removed under vacuum and the residue in 1% acetic acid was passed over a Bio-Rex 70 (H+) ion exchange column. The basic products are washed off the ion exchange column with pyridine buffer (H$_2$O/pyridine/HOAc, 66:30:4) and evaporated to give crude product.

EXAMPLE 10

Preparation of:

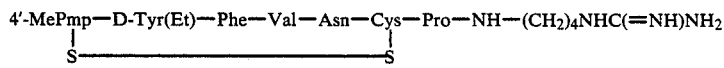

Mono-Boc-1,4-diaminobutane (1.25 g, 6.6 mmol), prepared from putrescine, in dioxane (2 ml) and water (6.5 ml) was treated with O-methylisourea hydrogen sulfate (1.25 g, 7.26 mmol) and 2N sodium hydroxide (aq) (3.75 ml) at room temperature. The resulting solution was stirred for 6 days. The solvent was removed under reduced pressure and the residue made basic (pH=12) by the addition of 2N sodium hydroxide. The residue was again evaporated, taken up in ethyl acetate, filtered and evaporated. The crude guanidine was dried by evaporation from toluene and used without further purification.

The crude guanidine (410 mg, 1.78 mmol) in 2N sodium hydroxide (aq) (2 ml) and water (2 ml) was treated at room temperature with p-toluenesulfonyl chloride (340 mq, 1.78 mmol) for 18 hours. The pH was adjusted to 8 with 5% sodium carbonate solution. The mixture was extracted with ethyl acetate to give, upon evaporation, 437 mg of crude product. Purification by flash chromatography (3×15 cm silica bed, 80% ethyl acetate/hexane) gave 265 mg (39%) of the desired tosylated product whose identity was confirmed by $^1$H NMR and CI-mass spectroscopy.

The Tos-NHC(=NH)NH(CH$_2$)$_4$-NH Boc (108 mg, 0.281 mmol) in methylene chloride (1 ml) was treated with trifluoroacetic acid (1 ml) at 0° for 40 minutes. The reaction was evaporated under vacuum, the residue adjusted to pH 8 with 5% sodium carbonate solution and evaporated to dryness. The residue was taken up into ethyl acetate, filtered and evaporated. The crude des-Boc product was dried by evaporation from toluene to give 66 mg (82%). Identity was confirmed by 'H NMR and used without further purification.

[1-(4'-Methyl-β-mercapto-β,β-cyclopentamethylene propionic acid)-2--D-(O-ethyl)tyrosine-4-valine-8-desarginine-9-desglycinamide]-vasopressin, prepared as in Example 8, in dimethylformamide is treated at room temperature with the tosylguanidinobutylamine. The mixture is stirred for 43 hours. The solvent is removed at reduced pressure and the residue is dissolved in trifluoroacetic acid, then treated at room temperature with trifluoromethanesulfonic acid and anisol with stirring for 2 hours. The reaction mixture is evaporated to dryness, dissolved in 10% acetic acid, filtered and passed through a Bio-Rex 70 column. The crude guanidine is eluted off the column with pyridine buffer (pyridine/water/acetic acid, 30:66:4), evaporated to afford the crude peptide.

propriate acid gives the respective peptide salt as follows:

[1-(4'-methyl-β-mercapto-β,β-cyclopentamethylene propionic acid)-2-tyrosine-3 -(4'-methylphenylalanine)-7-arginine-8-D-arginine-9-desglycine]-vasopressin acetate;

[1-(4'-methyl-β-mercapto-β,β-cyclopentamethylene propionic acid)-2-D-phenylalanine-4-isoleucine-7-arginine-8-D-arginine-9-desglycine]-vasopressin phosphate;

[1-(4'-methyl-β-mercapto-β,β-cyclopentamethylene propionic acid)-2-D-isoleucine-4-cyclohexylglycine-7-arginine-8-D-arginine-9-desglycine]-vasopressin hydrochloride.

EXAMPLE 13

The vasopressin antagonist compound 1-(4'-methyl-β-mercapto-β,β-cyclopentamethylenepropionic acid) 2 (O-ethyl)-D-tyrosine-4-valine-7-ornithine-8-ornithine 9-ornithine]-vasopressin is represented by the following structural formula:

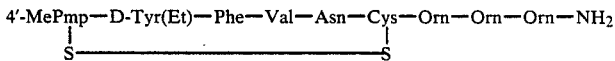

EXAMPLE 11

Substituting a stoichiometric quantity of Boc-L-Tyr(Et) for Boc-D-Tyr(Et) at the second unit of the peptide synthesis of Example 2 gives cyclized The protected peptide resin intermediate, 4'-MePmp(4-MeBzl)-D-Tyr(Et)-Phe-Val-Asn-Cys(4-MeBzl)-Orn(ClZ)-Orn(ClZ)-Orn(ClZ)-BHA is synthesized by solid-phase methods on the automated synthesizer Beckman 990 B using 1.0 g of benzhydrylamine

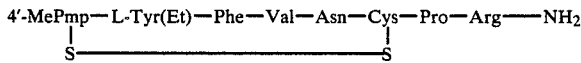

Substituting in Example 2, Boc-D-Ile for Boc-D-Tyr(Et) at the second unit gives

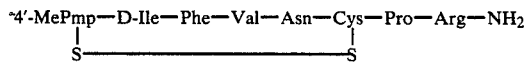

Substituting Boc-L-Phe(4 Me) for the amino acid at the third unit and Boc-Nle at the fourth unit in the synthesizer sequence reactions of Example 2 gives resin (approx. 0.62 mmol). All amino acids are protected as t-butyloxycarbonyl on the nitrogen and are activated by DCC/HBT for sequential coupling. The 4-MePmp(4-MeBzl) is coupled using DMAP/DCC. The peptide is cleaved from the resin with simultaneous deprotection of the side-chain protecting groups using anhydrous HF (30 ml) in the presence of anisole (3.0 ml) at 0° C. for 60 minutes. After evaporation in vacuo to dryness, the residue containing peptide is washed with anhydrous ether. The crude peptide is extracted with

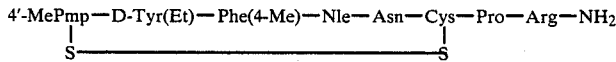

Substituting Boc-Cha at the fourth unit gives dimethylformamide (100 ml) and 40% acetic acid (100

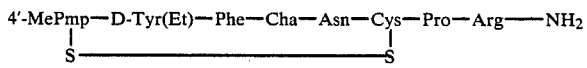

Substituting unprotected Gln at the fourth unit using HBT gives ml) and the extracts are added to 3.5 liters of degassed water. The aqueous diluted disulfhydryl nonapeptide

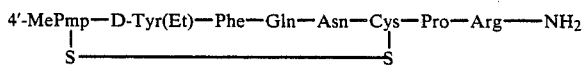

EXAMPLE 12

Substituting the appropriate protected ring units in the synthetic sequence of Example 7 and using the apmixture is oxidatively cyclized with 110 ml of potassium ferricyanide (0.01 M) at a pH of 7.2. The pH of the solution is adjusted to 4.5 using glacial acetic acid (HOAc). The solution is passed through a weakly acid acrylic resin (Bio-Rex 70) column. The column is eluted with pyridine acetate buffer (30:4:66, pyridine/glacial acetic acid/water v/v). The pyridine acetate was removed by distillation in vacuo. The residue is lyophilized from dilute acetic acid to give the product of partially purified crude peptide.

EXAMPLE 14

The vasopressin antagonist compound [1-(4'-methyl-β-mercapto-β,β-cyclopentamethylenepropionic acid)-2-(O-ethyl)-D-tyrosine-4-valine-7-lysine-8-lysine-9-lysine]-vasopressin is represented by the following structural formula:

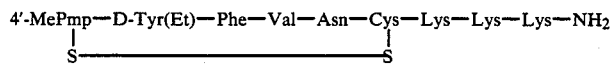

The protected peptide resin intermediate, 4'-MePmp(4-MeBzl)-D-Tyr(Et)-Phe-Val-Asn-Cys(4-MeBzl)-Lys(ClZ)-Lys(ClZ)-Lys(ClZ)-BHA is synthesized by solid-phase methods on the automated synthesizer Beckman 990 B using 1.0 g of benzhydrylamine resin (approx. 0.62 mmol). All amino acids are protected as t-butyloxycarbonyl on the nitrogen and are activated by DCC/HBT for sequential coupling. The 4-MePmp(4-MeBzl) is coupled using DMAP/DCC. The peptide is cleaved from the resin with simultaneous deprotection of the side-chain protecting groups using anhydrous HF (30 ml) in the presence of anisole (3.0 ml) at 0° for 60 minutes. After evaporation in vacuo to dryness, the residue containing peptide is washed with anhydrous ether. The crude peptide is extracted with dimethylformamide (100 ml) and 40% acetic acid (100 ml) and the extracts are added to 3.5 liters of degassed water. The aqueous diluted disulfhydryl nonapeptide mixture is oxidatively cyclized with 110 ml of potassium ferricyanide (0.01 M) at a pH of 7.2. The pH of the solution is adjusted to 4.5 using glacial acetic acid (HOAc). The solution is passed through a weakly acid acrylic resin (Bio-Rex 70) column. The column is eluted with pyridine acetate buffer (30:4:66, pyridine/glacial acetic acid/water v/v). The pyridine acetate is removed by distillation in vacuo. The residue is lyophilized from dilute acetic acid to give the product of partially purified crude peptide.

EXAMPLE 15

The vasopressin antagonist compound [1-(4'-methyl-β-mercapto-β,β-cyclopentamethylenepropionic acid)-2-(O-ethyl)-D-tyrosine-4-valine-8-arginine-9-arginine]-vasopressin is represented by the following structural formula:

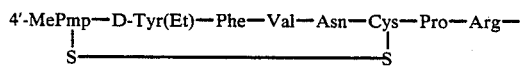

The protected peptide resin intermediate, 4'-MePmp(4-MeBzl)-D-Tyr(Et)-Phe-Val-Asn-Cys(4-MeBzl)-Pro-Arg(Tos)-Arg(Tos)-BHA is synthesized by solid phase methods on the automated synthesizer Beckman 990 B using 1.0 g of benzhydrylamine resin (approx. 0.62 mmol). All amino acids are protected as t-butyloxycarbonyl on the nitrogen and are activated by DCC/HBT for sequential coupling. The 4'-MePmp(4-MeBzl) is coupled using DMAP/DCC. The peptide is cleaved from the resin with simultaneous deprotection of the side-chain protecting groups using anhydrous HF (30 ml) in the presence of anisole (3.0 ml) at 0° C. for 60 minutes. After evaporation in vacuo to dryness, the residue containing peptide is washed with anhydrous ether. The crude peptide is extracted with dimethylformamide (100 ml) and 40% acetic acid (100 ml) and the extracts are added to 3.5 liters of degassed water. The aqueous diluted disulfhydryl nonapeptide mixture is oxidatively cyclized with 110 ml of potassium ferricyanide (0.01M) at a pH of 7.2. The pH of the solution is adjusted to 4.5 using glacial acetic acid (HOAc). The solution is passed through a weakly acid acrylic resin (Bio-Rex 70) column. The column is eluted with pyridine-acetate buffer (30:4:66, pyridine/glacial acetic acid/water v/v). The pyridine acetate is removed by distillation in vacuo. The residue is lyophilized from dilute acetic acid to give the product of partially purified crude peptide.

EXAMPLE 16

Parenteral Dosage Unit Compositions

A preparation which contains 0.10 mg of the peptide of Example 2 as a sterile dry powder for parenteral injection is prepared as follows: 0.5 mg of peptide is dissolved in 1 ml of an aqueous solution of 20 mg of mannitol. The solution is filtered under sterile conditions into a 2 ml ampoule and lyophilized. The reconstituted solution is administered to a patient in need of vasopressin antagonist treatment as necessary, from 1-5 times daily by injection, or in an equivalent continuous i.v. drip injection.

Nasal Dosage Unit Compositions 2.5 Mg of a finely ground peptide of this invention, such as the product of Example 3, is suspended in a mixture of 75 mg of benzyl alcohol and 1.395 g of a suspending agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to a subject in need thereof from 1-6 times a day.

What is claimed is:

1. A compound of the formula:

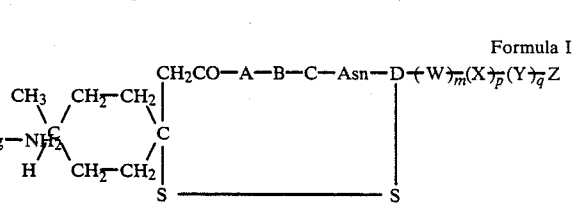

Formula I

A is D or L isomer of Phe, Phe(4'—Alk) Ile, Cha, Tyr, or Tyr(O—Alk);

B is Phe, Phe(4'—Alk), Tyr(O—Alk), Ile or Tyr;

C is Val, Ile, Abu, chg, Gln, Lys, Cha, Nle, Leu, Ala or Gly;
D is D or L isomer of Cys;
m, p and q are each 0 or 1;
W is D or L isomer of Pro, Arg, HArg, N-MeArg, Lys or Orn;
X is Gly or a D or L isomer of Arg, Orn or Gln, provided that when m is 0, X is not Gly;

Y is Gly or a D or L isomer of Arg, Lys, Orn, Ser,

Gln, Tyr or Ala, provided that if both m and p are 0, Y is not Gly;
Z is NH—(CH$_2$)$_n$—NHR, NHR', OH or a D or L isomer of Arg—NH$_2$, Lys—NH$_2$ or Orn—NH$_2$, provided that if m, p and q are 0, Z is not NHR' or OH;
R is H or C(=NH)—NH$_2$;
R' is H or Alk;
n is 2–6; and
Alk is alkyl having 1–4 carbon atoms;
or a pharmaceutically acceptable acid addition salt, or lower alkyl or benzyl ester thereof.

2. A compound of claim 1 which is the cis isomer of the 4'-methyl-β-mercapto-β,β-cyclopentamethylene-propionic acid moiety.

3. A compound of claim 1 in which A is D-Tyr or D-Tyr(Et); B is Phe; C is Val; m, p and q are each 0 or 1; W is a D or L isomer of Pro, Arg or N-MeArg; X is a D or L isomer of Arg or Gly; Y is Gly; and Z is NHR or a D or L isomer of Arg-NH$_2$, provided that X is not Gly when m is 0, and q is 0 if both m and p are 0.

4. A compound of claim 2 in which (W)$_m$-(X)$_p$-(Y)$_q$-Z is Pro-Arg-NH$_2$, Arg-Gly-NH$_2$, Pro-Arg-Gly-NH$_2$, Arg-D-Arg-NH$_2$, D-Arg-D-Arg-NH$_2$, Pro-NH(CH$_2$)$_4$NHC(=NH)-NH$_2$, N-MeArg-Arg-NH$_2$, Pro-Arg-NH(CH$_2$)$_2$NH$_2$, Arg-NH$_2$ or Arg-Gly-Arg-NH$_2$.

5. A compound of claim 2 in which (W)$_m$-(X)$_p$-(Y)$_q$-Z is Pro-Arg-NH$_2$.

6. A compound of claim 2 in which (W)$_m$-(X)$_p$-(Y)$_q$-Z is Pro-Arg-Gly-NH$_2$.

7. A compound of claim 2 in which (W)$_m$-(X)$_p$-(Y)$_q$-Z is Arg-D-Arg-NH$_2$.

8. A compound of claim 2 having the formula:

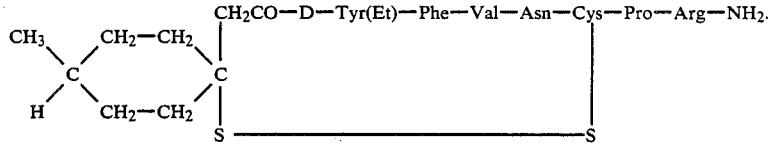

9. A compound of claim 2 having the formula:

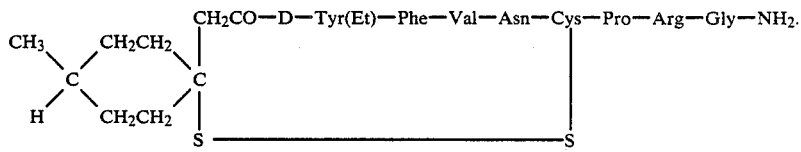

10. A compound of claim 2 having the formula:

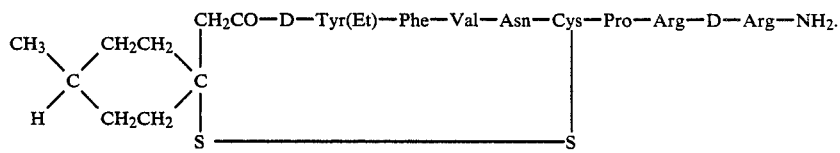

11. A pharmaceutical composition for producing vasopressin antagonist activity without substantial vasopressin agonist activity comprising a pharmaceutical carrier and an effective amount of a compound claim 1.

12. A pharmaceutical composition for producing vasopressin antagonist activity without substantial vasopressin agonist activity comprising a pharmaceutical carrier and an effective amount of a compound of claim 4.

13. A method of producing vasopressin antagonist activity without substantial vasopressin agonist activity in a patient in need thereof which comprises administering an effective amount of a compound of claim 1.

14. A method of claim 13 in which the administration is parenterally or intranasally.

15. A method of treating congestive heart failure, hypertension, hepatic cirrhosis, hyponatremia or primary dysmenorrhea in a patient in need thereof which comprises administering parenterally or intranasally to the patient an effective amount of a compound of claim 1.

16. A method of claim 15 in which within the compound (W)$_m$-(X)$_p$-(Y)$_q$-Z is Pro-Arg-NH$_2$, Arg-Gly-NH$_2$, Pro-Arg-Gly-NH$_2$, Arg-D-Arg-NH$_2$, D-Arg-D-Arg-NH$_2$, Pro-NH(CH$_2$)$_4$NHC(=NH)-NH$_2$, N-MeArg-Arg-NH$_2$, Pro-Arg-NH(CH$_2$)$_2$NH$_2$, Arg-NH$_2$ or Arg-Gly-Arg-NH$_2$.

* * * * *